United States Patent
Lillehoj et al.

(10) Patent No.: US 6,451,984 B1
(45) Date of Patent: Sep. 17, 2002

(54) CHICKEN MONOCLONAL ANTIBODIES SPECIFIC FOR COCCIDIAL ANTIGENS INVOLVED IN INVASION OF HOST LYMPHOCYTES

(75) Inventors: Hyun S. Lillehoj, West Friendship; B. Nichols Majorie, Columbia, both of MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 996 days.

(21) Appl. No.: 08/524,668

(22) Filed: Sep. 8, 1995

(51) Int. Cl.[7] .................... C07K 16/00; C12P 21/08
(52) U.S. Cl. ................ 530/388.6; 530/24.32; 424/151.1; 435/252.3; 435/240.27
(58) Field of Search ............. 435/240.27, 252.3; 424/88; 536/24.32; 530/388.6

(56) References Cited

U.S. PATENT DOCUMENTS

| | | | |
|---|---|---|---|
| 4,650,676 A | * 3/1987 | Schenkel et al. | 424/88 |
| 4,724,145 A | * 2/1988 | Murray et al. | 424/88 |
| 5,028,694 A | * 7/1991 | Mewman, Jr. et al. | 530/350 |
| 5,122,471 A | * 6/1992 | Jenkins et al. | 435/252.3 |
| 5,187,080 A | * 2/1993 | Andrews et al. | 435/69.3 |
| 5,273,901 A | * 12/1993 | Jacobson et al. | 435/243 |
| 5,279,960 A | * 1/1994 | Anderson et al. | 435/243 |
| 5,298,613 A | * 3/1994 | Chakraborty et al. | 536/24.32 |
| 5,403,548 A | * 4/1995 | Binger et al. | 424/191.1 |
| 5,411,881 A | * 5/1995 | Matsuda et al. | 435/240.27 |

OTHER PUBLICATIONS

H.S. Lillehoj et al, Pol. Sci., 1994, 73, pp. 1685–1693.*
Augustine, P.C. Proc. Soc. Exp Biol Med, Oct 1991, 198(1) pp 606–611.*
Trout et al, J. Parasitol, Oct 1993, 79(5), p709–2.*
Castle et al, J. Parasitol, Jun. 1991, 77(3), p 384–90.*
Taylor et al, J. Protozool, Nov.–Dec. 1990, 37(6) p 540–5.*
Augustine, P.C et al, J. Parasitol, Aug. 1988, 74(4), p 653–9.*
Danforth, H D, Avian Disease, Jan.–Mar. 1987, 31(1) p 99–104.*
Trout et al, Poult Sci, Jul. 1995, 74(7) p 1117–25 (abstract).*

* cited by examiner

*Primary Examiner*—L. F. Smith
*Assistant Examiner*—Ginny Allen Portner
(74) *Attorney, Agent, or Firm*—M. Howard Silverstein; John D. Fado; Janelle S. Graeter

(57) ABSTRACT

A stable chicken hybridoma secreting a monoclonal antibody (mAb) that detects the conoid structure of *Eimeria acervulina* (*E. acervulina*) sporozoites has been developed. The hybridoma is made by fusing a thymidine kinase (TK)-deficient chicken myeloma with spleen cells from chickens immunized with sporozoite antigen. The monoclonal antibody recognizes sporozoite proteins on the conoid of the anterior tip of *E. acervulina* sporozoites. The monoclonal antibody has been shown to inhibit the invasion of sporozoites into $CD8^+$ T cells in vitro thereby indicating its role in the recognition of host cells during the invasion process following infection with Eimeria parasites.

2 Claims, 5 Drawing Sheets

CHICKEN MONOCLONAL ANTIBODIES SPECIFIC FOR COCCIDIAL ANTIGENS INVOLVED IN INVASION OF HOST LYMPHOCYTES

BACKGROUND OF THE INVENTION

1. Field of the Invention

The successful development of a vaccine against coccidia parasites requires obtaining parasite antigens that can block parasite invasion of host lymphocytes and prevent intracellular development or antigens that are sufficiently immunogenic in chickens to provide protection from infection. Identification of these antigens has been difficult to achieve, however, and the coccidia parasite antigens that interact with chicken lymphocytes have not previously been identified. Mouse monoclonal antibodies, although they have been available since 1985, are not effective for identifying coccidial antigens important in chickens since chickens recognize different antigenic determinants from mice. This invention relates to chicken hybridomas which secrete anti-coccidia monoclonal antibodies specific for antigens involved in parasite-host lymphocyte interactions. These antigens are important in the development of anti-coccidial vaccines as well as in the detection of coccidia parasites in infected animals.

2. Description of the Prior Art

Avian coccidiosis is caused by an intracellular protozoan parasite belonging to the genus Eimeria which infects the intestinal mucosa of livestock and poultry and seriously impairs the growth and feed utilization of the infected animals. The disease causes annual losses in the poultry industry of $440 million world wide. Identification of parasite antigens involved in the invasion of host lymphocytes is crucial for the development of coccidial vaccines, since sporozoite invasion of host lymphocytes is the first step involved in coccidiosis.

Mouse monoclonal antibodies (mAbs) have been used to characterize coccidial antigens (Danforth, H. D. 1983. *Am. J. Vet. Res.* vol. 44, pp. 1722–1727; Speer et al. 1983. *J. Protozool.* vol. 30, pp. 548–554) and to identify cDNAs encoding recombinant proteins of Eimerian parasites (Castel et al. 1991. *J. Parasitol.* vol. 77, pp. 384–390; Ko et al. 1990. *Mol. Biochem. Parasitol.* vol. 41, pp. 53–64). The use of these recombinant proteins as vaccines, however, has produced only limited success, and the use of mouse mAbs to define epitopes important in the chicken's immune response to Eimeria is debatable since differences have been reported in the recognition of target antigens by immune sera from chickens, rabbits and mice (Jenkins and Dame. 1987. *Mol. Biochem. Parasitol.* vol. 25, pp. 155–164).

Nishinaka et al. (1991. *J. Immunol. Methods.* vol. 139, pp. 217–222, herein incorporated by reference) described a cell line for producing hybridomas from chicken cells, i.e. a chicken B cell line deficient in thymidine kinase activity fused with spleen cells of chickens immunized with keyhole limpet hemocyanin. The monoclonal antibodies produced by these cells, however, were suggested for use in clinical applications where the capability of avoiding reactivity with mammalian IgGs and activation of human complement systems would be important. There has been no suggestion of their use in elucidating immunological reactions in avian systems.

Thus, the need has continued for providing means for detecting and selecting for coccidia parasite antigens involved in the infection of host lymphocytes and capable of conferring protection against infection by Eimerian parasites.

SUMMARY OF THE INVENTION

We have discovered that monoclonal antibodies from chicken hybridomas are effective for identifying parasite antigens involved in the infection and invasion of host lymphocytes. In addition, these antigens are also useful for detecting the occurrence of parasite infection and for detecting the presence of parasites in a sample.

In accordance with this discovery, it is an object of the invention to provide a novel chicken monoclonal antibody which is specific for Eimeria antigens involved in host cell invasion and thus capable of detecting sporozoite antigens involved in host lymphocyte invasion.

It is also an object of the invention to provide a hybridoma cell line which produces the novel chicken monoclonal antibody.

Other objects and advantages of the invention will become readily apparent from the following description.

DETAILED DESCRIPTION OF THE INVENTION

Figure 1A:
FIGS. 1A & B show the indirect immunofluorescence staining of *Eimeria acervulina* (*E. acervulina*) sporozoites with mAb 6D-12-G10.

Hybridomas which secrete monoclonal antibodies specific for *E. acervulina* antigens involved in host lymphocyte invasion and infection are produced by fusing lymphocytes from chickens immunized with *E. acervulina* antigens with chicken myeloma cells (described by Nishinaka et al., supra). The chicken myeloma cells are derived from a chicken B cell line (HU3R27) deficient in thymidine kinase activity fused with spleen cells from a chicken immunized with Newcastle disease virus. The lymphocytes are obtained by either 1) oral infection of 6- to 12-week-old chicks with *E. acervulina* followed by collection of peripheral blood lymphocytes (as described by Lillehoj et al. 1994. *Poultry Science.* vol. 73, pp. 1685–1693. herein incorporated by reference) or 2) intramuscular injection of 6- to 12-week-old chicks with $CD8^+$ T cells having been incubated with *E.*

*acervulina* sporozoite antigen followed by collection of spleens and preparation of spleen cells (this procedure is described in detail in Examples I–III). The lymphocytes thus obtained are fused with R27H4 non-secreting chicken myeloma cells in polyethylene glycol 4000. The fused cells are suspended in hypoxanthine-aminopterin-thymidine (HAT)-supplemented medium and plated in 96-well microculture plates. After incubation of about 2 weeks, culture supernatants from hybrid clones are screened for their binding activity against sporozoite antigens and those hybridomas secreting the mAbs having desired specificities are selected. Selected hybridomas are cloned and plated with irradiated spleen cells as feeder cells for single cell cloning.

One stable hybridoma cell line was selected, and the mAb was tested for antigen specificity. The mAb was given the designation 6D-12-G10. MAb 6D-12-G10 recognizes antigens located at the anterior tip of sporozoites as demonstrated by the presence of intense fluorescent staining by immunofluorescence assay (IFA). In addition, it was shown that the mAb recognizes coccidial antigens associated with conoid complex by electronmicroscopy. Staining of sporozoites with gold-labeled rabbit anti-chicken immunoglobulin revealed localization of the mAb on target antigens on the conoid at the anterior portion. The molecular weights of the antigen recognized were 20 and 21 kDa under reducing and non-reducing conditions, respectively, by Western blot analysis. It was also shown that the mAb showed a significant inhibition of the invasion of *E. acervulina* sporozoites into $CD8^+$ T cells in vitro.

The mAb is useful for immunological procedures including detection of sporozoite- and/or merozoite-stage Eimerian parasites when used according to the specificities described above. Detection may be carried out by any immunoassay method known in the art such as radioimmunoassay, enzyme-linked immunoassay, fluorescent immunoassay, etc. In addition, the mAb is particularly useful for the separation and purification of the antigens for which they are specific. This procedure may successfully be carried out by known immunological separation methods well-known in the art such as affinity chromatography where mAb comprises the solid phase. This application is particularly important in view of the implications of the antigen's involvement in infection of host lymphocytes.

The events associated with invasion of many Apicomplexa parasites include: 1) attachment to host cells; 2) protrusion of the conoid; 3) formation of a moving junction that moves posteriorly as the parasite enters the host cell; 4) microneme exocytosis; 5) rhoptry exocytosis; and 6) gliding of the parasite into the vacuole (Dubremetz and Schwartzman. 1993. *Res. Immunol*. vol. 144, pp. 31–33; Schwartzman and Saffer. 1992. *Subcell. Biochem*. vol. 18, pp. 333–364). Although the detailed events during attachment and invasion of host cells by Eimerian parasites have not been identified, it has been reported that sporozoites rapidly enter $CD8^+$ T cells in the intestinal epithelium following oral infection and are subsequently transported by these cells to the crypt epithelium where they further develop (Trout and Lillehoj. 1993. *J. Parasitol*. vol. 73, pp. 790–792). Specific parasite ligand-host cell receptor interactions similar to those of other members of the phylum Apicomplexa are believed to occur (Joiner and Dubremetz. 1993. *Infect. Immunity*. vol. 61, pp. 1169–1172; Perkins, M. E. 1992. *Parasitology Today*. vol. 8, pp. 28–32; Russell and Burns. 1984. *J. Cell Sci*. vol. 65, pp. 193–207; Werk, R. 1985. *Rev. Infect. Dis*. vol. 7, pp. 449–457), as for example in Plasmodium, a coccidian parasite closely related to Eimeria, where micronemes and rhoptries have been implicated in parasite attachment and invasion (Perkins, supra).

The conoid, a basket-like meshwork of spirally woven raicrotubules (D'Haese et al. 1977. *Avian Pathol*. vol.22, pp. 3–21), aids in the penetration of host cells. Since infective stages routinely enter cells apical end first (Long, P. L. 1982. *The Biology of the Coccidia*. University Park Press, Baltimore, Md.), an extended conoid, coupled with secretions from the rhoptries and micronemes is believed to facilitate entrance into the cell (Werk, supra). Thus, mAb 6D-12-G10-mediated inhibition of entry of sporozoites into $CD8^+$ T cells in vitro supports the contention that the antigens of the conoid play a role in the parasite's recognition and initial adherence to the host cells. With the production of monoclonal antibodies capable of detecting the conoid complex, isolation of conoid protein makes possible studies to further elucidate the role of conoid in host cell invasion.

Eimeria parasites, once excysted in the gut, interact closely with intestinal $CD8^+$ lymphocytes (Lillehoj and Trout. 1994. *Parasitology Today*. vol. 10, pp. 10–13; Trout and Lillehoj, supra). Most of the sporozoites are found within $CD8^+$ T cells, and some in macrophages, in the intraepithelium and are then transported to the crypt epithelium (Trout and Lillehoj, supra). In chickens immune to *E. tenella*, inhibition of sporozoite transfer from intraepithelial lymphocytes to crypt enterocytes was seen (Rose et al. 1984. *Parasitology*. vol. 88, pp. 199–210). Since mAb 6D-12-G10 inhibits sporozoite invasion of host $CD8^+$ lymphocytes in vitro, the coccidial antigens recognized by this mAb are believed to play an important role during invasion and the host immune response to coccidia.

The following examples are intended only to further illustrate the invention by exemplifying the preparation of mAb 6D-12-G10. The examples are not intended to limit the scope of the invention as defined by the claims.

EXAMPLES

Example I
Preparation of Sporozoite Antigens

Sporulated oocysts of *Eimeria acervulina* (#84 USDA strain) were collected using the technique described by Ryley et al. (1976. *Parasitoloy*. vol. 73, pp. 311–326, herein incorporated by reference). Sporozoites were prepared by excysting the sporocysts in a solution containing 0.125% (wt/vol) trypsin (Sigma Chemical Co., St. Louis, Mo.) and 1% (wt/vol) taurodeoxycholic acid in Hanks' Balanced Salt Solution (HBSS), pH 7.6 for 10 minutes at 41° C. in a 5% $CO_2$ incubator. Sporozoites were separated from cellular debris on DEAE (DE52, Whatman Paper Ltd., Clifton, N.J.) cellulose columns (Schmatz et al. 1984. *J. Protozool*. vol. 31, pp. 181–183).

Pelleted sporozoites ($10^9$/ml) in phosphate buffered saline (PBS) were freeze-thawed six times with dry ice and warming to room temperature, then sonicated at 4° C. with a Microson Ultrasonic Cell Disrupter (Heat System, Framindale, N.Y. 11735).

Example II
Production of $CD8^+$ Cells

Embryonated eggs of White Leghorn crosses ($SC^R$) obtained as fertile eggs from a commercial breeder (HyLine International, Dallas Center, Iowa) were hatched and maintained in brooders until three weeks of age, at which time they were kept in wire colony cages. Chickens were housed in clean wire-floored cages taking special care not to be exposed to specific pathogens. Food and water were available ad libitum.

Spleens were obtained from 6–8 week-old SC chickens and macerated with a syringe plunger through a screen sieve in HBSS. The single cell suspension was overlayered onto Histopaque 1077 density gradient medium (Sigma Chemical Co., St. Louis, Mo.) and centrifuged at 1800 rpm for 20 minutes at room temperature. Lymphocytes at the interface were removed with a Pasteur pipet and washed 3 times in HBSS. Production of CD8+ T cell hybridomas was carried out by fusing spleen lymphocytes with R27H4 chicken lymphoma cells in polyethylene glycol 4000 as described by Nishinaka et al., supra. The hybridomas were resuspended in Iscove's modified Dulbecco's medium (IMDM) supplemented with 10% fetal calf serum (FCS) and hypoxanthine-aminopterin-thymidine (HAT, Sigma Chemical Co., St. Louis, Mo.) and plated in U-bottom 96-well microculture plates. After 10–14 days, wells showing growth were transferred to 24-well plates and expanded in IMDM supplemented with 10% FCS (IMDM-10) and hypoxanthine-thymidine. When hybridomas showed confluency, half of the cells from positive wells were analyzed by flow cytometry with a monoclonal antibody detecting the CD8 antigen as described by Lillehoj et al. (1988. *Eur. J. Immunology*. vol. 18, pp. 2059–2065, herein incorporated by reference). The stained cells were analyzed using an EPICS Profile II flow cytometer (Coulter Corporation, Hialeah, Fla.). For each hybridoma, $10^4$ viable cells were analyzed. CD8+ T-cell hybridomas were cloned by limiting dilution using irradiated spleen cells ($2 \times 10^6$ per well) as feeder cells. Hybridomas expressing the CD8 antigen were grown and aliquots frozen for further use.

Example III
Preparation of Hybridomas

Chickens at 6 to 12 weeks of age were given an intramuscular injection with $10^8$ CD8+ T cells which were incubated with soluble antigen prepared from *E. acervulina* sporozoites ($10^7$), as described in Example I, in 1 ml of IMDM supplemented with 10% FCS for 2 hrs at 37° C. with agitation. After washing 3 times, $10^8$ CD8+ T cells were resuspended in 0.5 ml HBSS, emulsified in 0.5 ml Freund's complete adjuvant and injected intramuscularly into 6-12-week-old chickens. A second injection with the same preparation was given in Freund's incomplete adjuvant and additional immunizations were given by intravenous injection with the same preparation without adjuvant at 1 week intervals. A final boost was given intravenously 3 days before splenectomy and cell fusion were carried out.

Production of hybridomas was carried out as described by Nishinaka et al., supra. Briefly, three days after the last immunization, single cell suspensions of spleens were prepared by centrifuging spleen cells for 20 min at 500×g on a Ficoll-Paque density gradient at 20° C. The cell fusion was carried out as described (Lillehoj et al., 1994, supra) using the R27H4 non-secreting chicken myeloma cell line in polyethylene glycol 4000. The fused cells were suspended in IMDM-10 supplemented with HAT and plated in 96-well microculture plates. After 2 weeks, culture supernatants from hybrid clones were screened using an enzyme-linked immunosorbent assay (ELISA) with sporozoite antigens prepared in Example I on the solid phase (Lillehoj and Ruff. 1986. *Avian Dis*. vol. 31, pp. 112–119). Hybridomas secreting the mAbs of interest were cloned by limiting dilution using irradiated spleen cells ($2 \times 10^6$ per well) as feeder cells. Undiluted culture supernatant from hybridomas were used in all experiments for the determination of specificity and binding properties. For blocking of sporozoite invasion of CD8+ cells, hybridoma supernatants were concentrated 100× using a Centriprep-100 concentrator with a molecular weight cut-off of 10 kDa (Amicon In., Beverly, Mass.). As a control, culture supernatant from R27 myeloma cells, diluted normal chicken serum concentrated as above were used. Protein concentration of concentrated samples were 100 mg/ml as measured by protein determination kit (Sigma Chemical Co., St. Louis, Mo.).

Example IV
Immunofluorescence

Air-dried sporozoites ($10^6$) on a clean glass slide were incubated with 100 µl of mAb for 40 minutes at room temperature. The slides were washed three times with PBS for 5 minutes and incubated with 50 µl of FITC-conjugated rabbit anti-chicken IgG (1:50, Sigma Chemical Co., St. Louis, Mo.) for 30 minutes. The slides were washed three times and counterstained with 0.01% Evans blue. Slides were mounted using Vectashield Mounting Medium (Vector Laboratories, Inc., Burlingame, Calif.) photographed using an epi-fluorescence microscope (Carl Zeiss, Germany) equipped with a 40× oil objective and a Texas Red/FITC dual wavelength filter set. Photomicrographs were taken using Kodak Tri-X pan 400 black and white negative film.

Figure 1B:
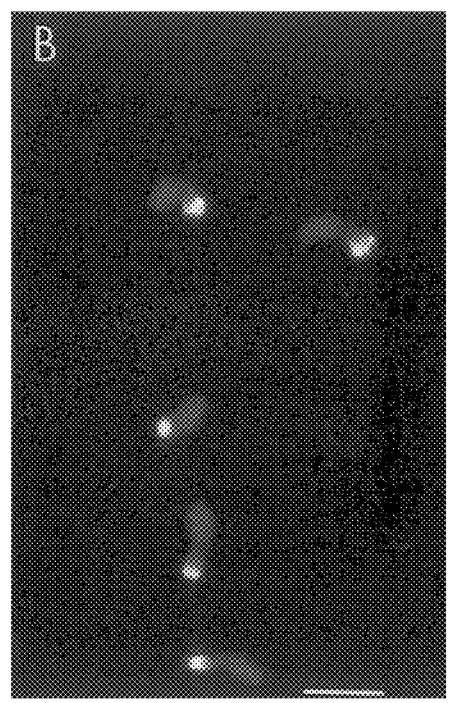

Culture supernatant containing mAb 6D-12-G10 intensely stained the tip end of *E. acervulina* sporozoites by IFA (FIG. 1) Culture supernatant from the control R27H4 myeloma did not stain *E. acervulina* sporozoites under the same condition.

Example V
Immunoelectron Microscopy

Figure 2:
FIG. 2 shows immunogold labeling of *E. acervulina* sporozoites with mAb 6D-12-G10.

*E. acervulina* sporozoites were fixed in 2% gluteraldehyde-4% paraformaldehyde-0.1 M PBS, pH 7.4, washed with 0.1 M PBS, dehydrated in a graded series of ethanols and embedded in LR White resin (PolySciences Inc., Warrington, Pa.) as described by Uni et al. (Uni et al. 1987. *Am. J. Troy. Med. Hyg*. vol. 36, pp. 481–488). Thin sections were cut with a diamond knife and mounted on nickel grid. Sections were incubated with PBS containing 0.1 M glycine, 1% bovine serum albumin (BSA), for 10 min. and PBS containing 1% nonfat dry milk, 0.5% BSA (PBS-NFDM-BSA), for 30 min to block non-specific binding. Grids were stained with mAb for 2 hours, rinsed with PBS-NFDN-BSA and incubated with colloidal gold conjugated rabbit anti-chicken IgG (15 nm diameter; E-Y Laboratories, San Mateo, Calif.) diluted 1:12.5 in PBS-NFDM-BSA. Grids were rinsed with PBS-NFDM-BSA and distilled water, dried, stained with 2% uranyl acetate and examined using a Hitachi 500H electron microscope (Hitachi Instrument Inc, San Jose, Calif.). Sporozoites stained the mAb 6D-12-G10 showed intense gold particle localization only on the conoid structure of apical complex (FIG. 2).

Example VI
Determination of Molecular Weight The size of the target coccidial antigens recognized by the mAb 6D-12-G10 were determined by Western blotting. Briefly, 10 µl of *E. acervulina* sporozoite antigens were resuspended in an equal volume of 2×SDS-PAGE sample buffer (125 mM Tris, 4% SDS, 20% glycerol, 10% beta-mercaptoethanol), heated at 100° C. for 4 min and resolved on a 4% stacking/12% resolving polyacrylamide gel at constant voltage (100V for stacking gel; 150V for resolving gel; Laemmli, U. K. 1970. *Nature*. vol. 277, pp. 680–682). The separated proteins were transblotted to Immobilon-P membrane (Millipore, Bedford, Mass.) using the Trans-Blot Electrophoretic Transfer Cell in transfer buffer (50 mM Tris, 380 mM glycine, 0.1% SDS, 20% methanol) for 3 hrs at 70V constant voltage (Towbin et al. 1979. *Proc. Natl. Acad. Sci. USA*. vol. 79, pp. 4350–4354). After transblotting, the membrane was treated for 18 hrs at 4° C. with PBS containing 1% nonfat dry milk (PBS-NFDM) to block non-specific binding. After blocking, individual lanes were stained for 2 hrs at room temperature with hydridoma supernatant or a 1:400 dilution of chicken normal serum as control and washed with PBS-NFDM for 30 min. Bound antibody was detected with biotin-labeled rabbit anti-chicken IgG (1:100, Sigma Chemical Co., St. Louis, Mo.) for 2 hours, avidin-peroxidase (1:500) for 30 min, and diaminobenzidine substrate (Sigma Chemical Co., St. Louis, Mo.). Molecular weights were estimated using biotinylated molecular weight standard proteins.

Figure 3:
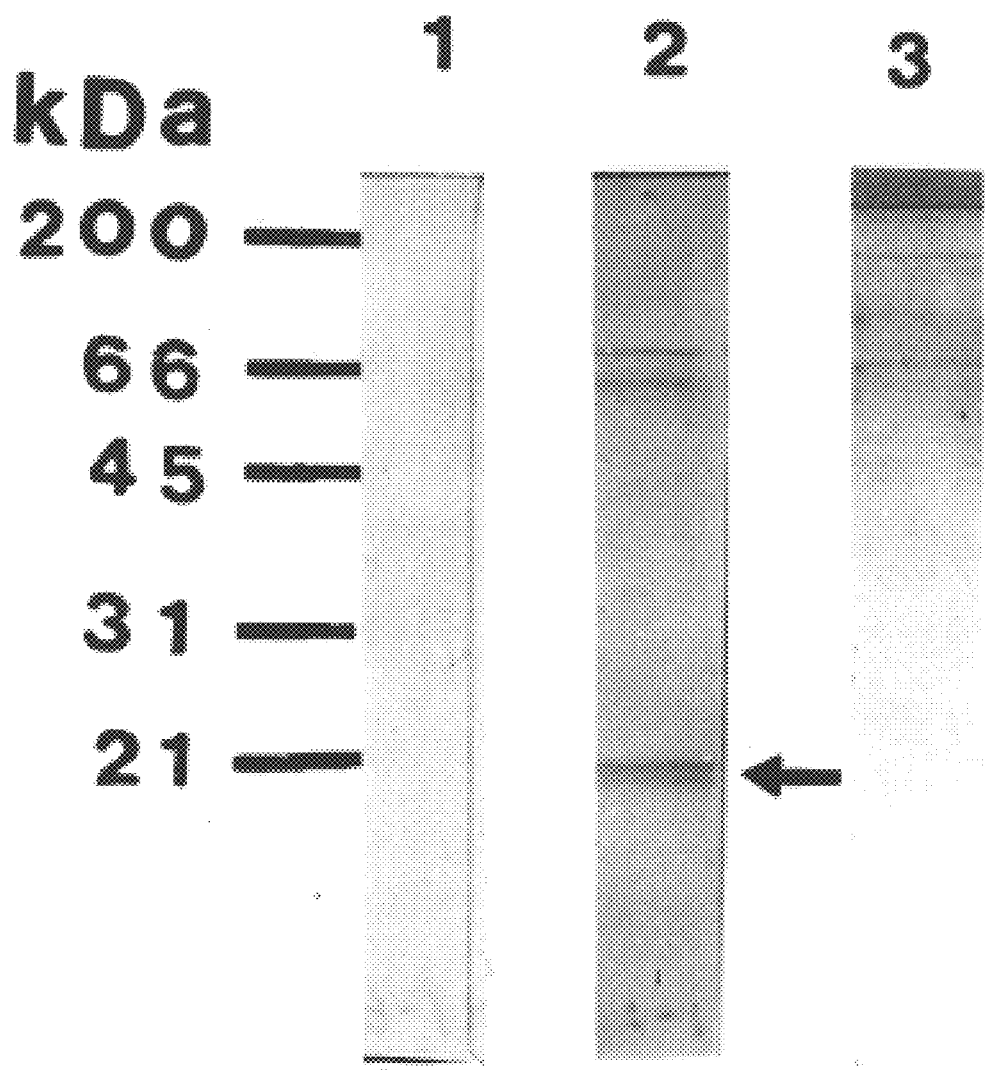
FIG. 3 shows Western blotting analysis of *E. acervulina* sporozoite antigens recognized by mAb 6D-12-G10. Sporozoite proteins were stained with mAb 6D-12-G10 (lane 2). No band was recognized by the control R27H4 myeloma supernatant (lane 1) or by control normal chicken serum (lane 3).

Under both reducing and non-reducing conditions, mAb 6D-12-G10 identified two sporozoite proteins of 20 and 21 kDa (FIG. 3, lane 2). No band was recognized by the control R27H4 myeloma supernatant (lane 1) or by control normal chicken serum (lane 3).

Example VII

Blocking of Sporozoite Invasion of $CD8^+$ Cells with mAb

Figure 4A:
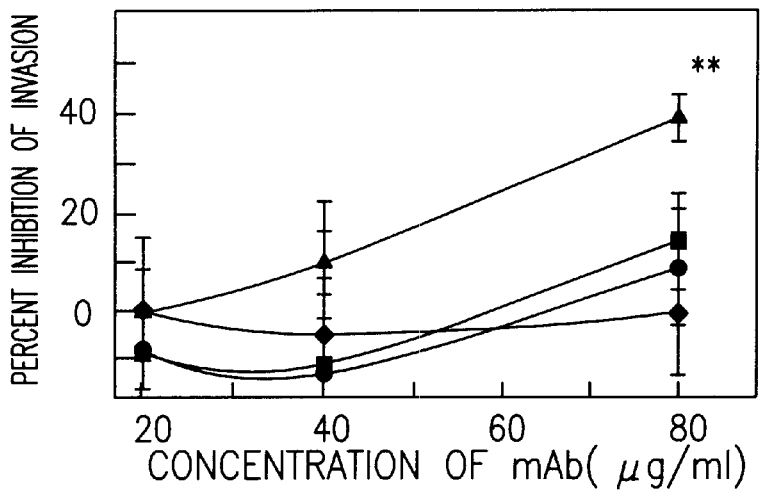
FIGS. 4A, B & C show the results of an in vitro sporozoite invasion blocking experiment 18 hours post-infection. *E. acervulina* sporozoites were pretreated with 20 $\mu$l, 40 $\mu$l or 80 $\mu$l concentrated mAb supernatant, control R27 myeloma supernatant or normal serum diluted with R27H4 myeloma supernatant for 1 hr (panel A), 2 hr (panel B) or 4 hr (panel C). Results for monoclonal antibody 6D-12-G10 (▲), 1:50 diluted normal serum (♦), 1:100 diluted normal serum (●) and 1:400 diluted normal serum (■) are shown. ** indicates a significant difference (P<0.01) from control.
Figure 4B:
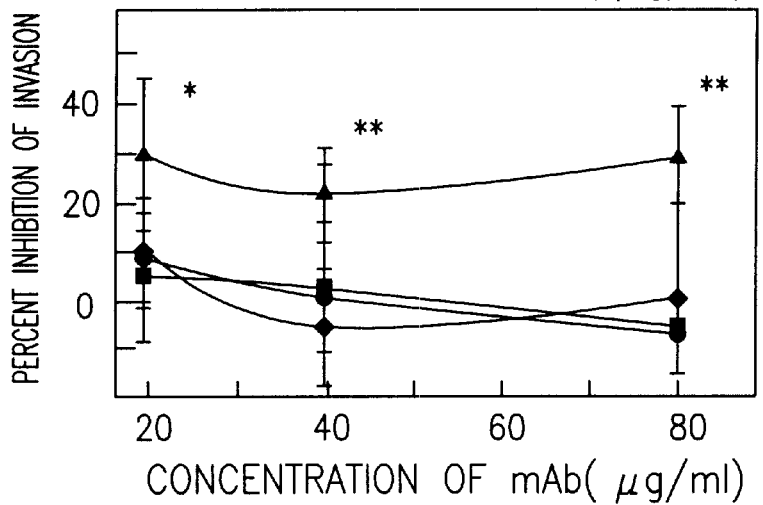
Figure 4C:
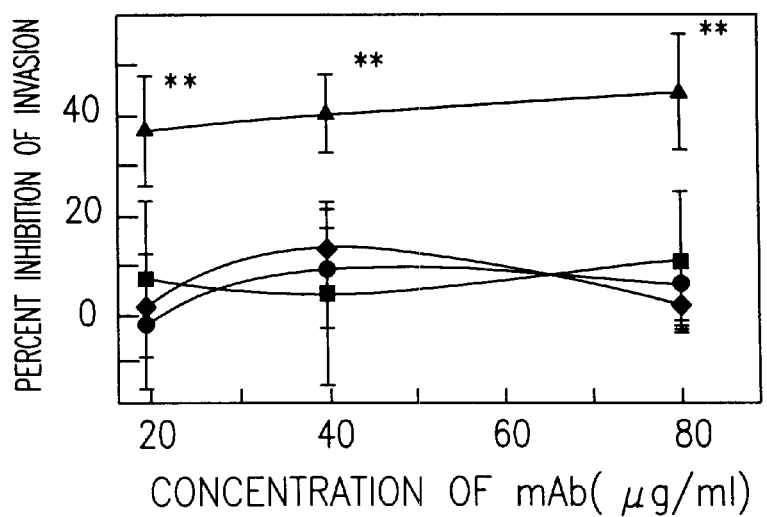

Freshly prepared *E. acervulina* sporozoites ($10^6$) were pretreated by incubating with 0.5 ml of IMDM-10 containing 20 µl, 40 µl or 80 µl of concentrated mAb supernatant, control R27 myeloma supernatant, or normal serum diluted with R27H4 myeloma supernatant (1:50, 1:100 and 1:400) at 37° C. for 1 (FIG. 4A), 2 (FIG. 4B) or 4 hr (FIG. 4C) with agitation. After pretreatment, $10^6$ $CD8^+$ T cells in 0.5 ml of IMDM-10 were infected with mAb pretreated sporozoites in 24-well plates at 41° C., 5% $CO_2$ for 4 hr (FIG. 5) or 18 hr (FIG. 4). After incubation, cell suspensions were mixed with 1 ml of 30% Percoll solution and overlayered on a 40/64% Percoll discontinuous gradient and centrifuged at 500×g for 20 min at 20° C. The majority of cells infected with sporozoites located at the 30/40% interface were resuspended in 100 µl of FCS. To assess the effect of mAb on sporozoite invasion, a cyto-spin smear was prepared from 50 µl of cell suspension and the cells stained with anti-sporozoite mAb (Hybridoma HB-8335, ATCC, Rockville, Md.) conjugated to FITC in 0.01% Evan's blue. The number of sporozoites within 500 $CD8^+$ T cells were counted and the percent inhibition of infection was calculated by the following formula: (1-mAb-treated/control)×100%.

Figure 5:
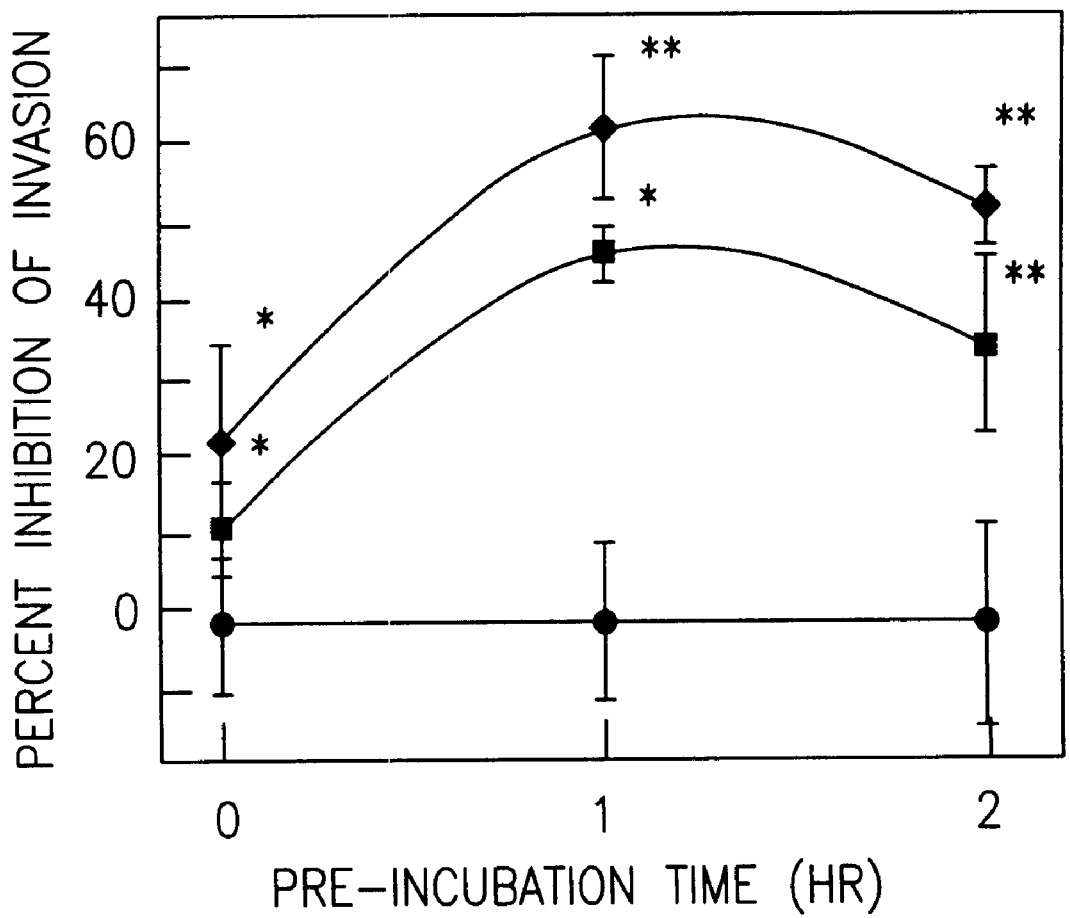
FIG. 5 shows the results of an in vitro sporozoite invasion blocking experiment after 4 hours post-infection. *E. acervulina* sporozoites were pretreated as described in FIG. 4. Results for monoclonal antibody 6D-12-G10 at 80 l/ml (■) 160 l/ml (♦) and 1:50 normal serum (●) are shown. ** indicate a significant difference (P<0.01) from control.

The mean sporozoite counts of samples in the blocking assays were compared by using the Student's t test. MAb 6D-12-G10 showed about 40% inhibition of the invasion of *E. acervulina* sporozoites into $CD8^+$ T cells compared to control supernatant (FIG. 4A and 4B). Normal chicken serum did not inhibit sporozoite invasion of $CD8^+$ T cells when tested at several dilutions. Pretreatment of sporozoites for 4 hr strongly inhibited sporozoite invasion of $CD8^+$ T cells in a dose-dependant manner. The similar results were obtained when sporozoites were pretreated 2 hr (FIG. 5).

We claim:

1. A chicken monoclonal antibody specific for *Eimeria acervulina* antigens involved in host cell invasion, wherein said antigens are located on the conoid of the anterior tip of *Eimeria acervulina* sporozoites.

2. A chicken hybridoma which secretes the monoclonal antibody of claim 1.

\* \* \* \* \*